(12) United States Patent
Geerligs et al.

(10) Patent No.: US 7,041,299 B2
(45) Date of Patent: May 9, 2006

(54) ESCAPE MUTANTS OF NEWCASTLE DISEASE VIRUS AS MARKER VACCINES

(75) Inventors: Harmen J. Geerligs, Weesp (NL); Ian Hamer Brown, Sandhurst (GB); Dennis John Alexander, Pyrford (GB); Michael Sinclair Collins, Byfleet (GB)

(73) Assignee: Wyeth, Madison, NJ (US)

( * ) Notice: Subject to any disclaimer, the term of this patent is extended or adjusted under 35 U.S.C. 154(b) by 129 days.

(21) Appl. No.: 10/990,204

(22) Filed: Nov. 16, 2004

(65) Prior Publication Data

US 2005/0069561 A1    Mar. 31, 2005

Related U.S. Application Data

(63) Continuation of application No. 10/725,841, filed on Dec. 2, 2003, now Pat. No. 6,833,133.

(60) Provisional application No. 60/471,419, filed on May 15, 2003, provisional application No. 60/431,519, filed on Dec. 6, 2002.

(51) Int. Cl.
 *A61K 39/17* (2006.01)
 *C07K 1/00* (2006.01)

(52) U.S. Cl. .................................. 424/214.1; 530/350

(58) Field of Classification Search ............. 424/186.1, 424/214.1, 236, 237, 239; 235/235.1; 530/350
See application file for complete search history.

(56) References Cited

U.S. PATENT DOCUMENTS

| | | | |
|---|---|---|---|
| 5,149,530 A | 9/1992 | van Wiltenburg | |
| 5,250,298 A | 10/1993 | Gelb, Jr. | |
| 5,733,556 A | 3/1998 | Schrier et al. | |
| 5,750,111 A | 5/1998 | Schrier | |
| 6,348,197 B1 | 2/2002 | Davelaar | |
| 6,719,979 B1 | 4/2004 | Peeters et al. | |
| 2004/0043035 A1* | 3/2004 | Mebatsion et al. | ...... 424/186.1 |

FOREIGN PATENT DOCUMENTS

| | | |
|---|---|---|
| WO | WO 9902695 A2 * | 1/1999 |
| WO | WO 02/36617 A2 | 5/2002 |

OTHER PUBLICATIONS

Mebatsion, T. et al. Newcastle Disease Virus (NDV) Marker Vaccine: an Immunodominant Epitope on the Nucleoprotein Gene of NDV Can Be Deleted or Reaplcaed by a Foreign Epitope (Oct. 2002) Journal of Virology, 76(20): 10138-10146.*

Peeters, B. et al. Generation of a recombinant chimeric Newcastle disease virus vaccine that allows serological differentiation between vaccinated and infected animals (2001) Vaccine, 19:1616-1627.*

J. gen. Virol. (1989), 70, 3105-3109, Printed in Great Britain, Location of Neutralizing Epitopes on the Fusion Protein of Newcastle Disease Virus Strain Beaudette C., K. Yusoff, et al.

* cited by examiner

*Primary Examiner*—James Housel
*Assistant Examiner*—M. Franco Salvoza
(74) *Attorney, Agent, or Firm*—John F. Levis

(57) ABSTRACT

A vaccine against Newcastle Disease contains one or more mutant immunogens of the NDW strain. The mutant immunogen lacks the antigenic binding site on the F glycoprotein which is recognized by the monoclonal antibody mAb 54. Reagent kits and assay methods help to distinguish vaccinated members of a poultry flock from those that may have been infected with wild-type Newcastle Disease virus.

1 Claim, No Drawings

US 7,041,299 B2

ESCAPE MUTANTS OF NEWCASTLE DISEASE VIRUS AS MARKER VACCINES

This application is a continuation of U.S. patent application Ser. No. 10/725,841, filed Dec. 2, 2003, now U.S. Pat. No. 6,833,133; which claims benefit of U.S. patent application No. 60/471,419, filed May 15, 2003, and claims benefit of U.S. patent application No. 60/431,519, filed Dec. 6, 2002.

FIELD OF THE INVENTION

The present invention is directed to a novel vaccine, and to a method of protecting poultry against Newcastle disease. More particularly, the invention relates to a safe and effective marker vaccine against Newcastle disease, and to reagent kits and assay methods for testing poultry that will furthermore permit poultry keepers to distinguish vaccinated members of the flock from those that may have been infected with the wild-type Newcastle disease virus. The invention also relates to novel mutant immunogens useful in a vaccine against Newcastle disease.

BACKGROUND OF THE INVENTION

Newcastle disease (ND) is a serious illness of poultry which is often times fatal, and therefore can result in significant economic losses. The ailment is caused by the Newcastle disease virus (NDV), a virus belonging to the genus Paramyxovirus of the family Paramyxovirdae. Within the avian paramyxoviruses, 9 distinct serotypes designated PMV-1 to PMV-9 are recognized; NDV is PMV-1 or serotype 1. A strain of NDV has now been designated "Wiltenberg" (also "Wiltenburg"), or NDW strain, as per U.S. Pat. No. 5,149,530, incorporated herein by reference.

From the viral envelope of NDV two types of surface projections (spikes) protrude. One is composed of a glycosylated protein which encompasses both hemagglutinating (H) and the neuraminidase (N) activity of the virion (HN glycoprotein). The other consists of glycoprotein F which is responsible for cell fusion, hemolysis and virus penetration. The carbohydrate-free matrix protein M which is incorporated into the inner side of the membrane, serves as a binding site for the nucleocapsid and is probably involved in the aggregation of the HN and F glycoproteins during virus budding from the plasma membrane.

Antibodies that greatly mediate immunity are produced against all three proteins. Those directed against the HN or F protein alone are protective.

Newcastle disease affects many commercial domestic poultry members, including chickens, turkeys, pheasants, guinea fowl, ducks, geese and pigeons. In addition, it can also afflict a wide range of captive and free-ranging semi-domestic and free-living birds including migratory waterfowl. Caged or aviary birds can also be affected.

The Newcastle disease virus enters the animal's body via the respiratory and intestinal tract. Air-borne particles of less than 5 microns disperse in the entire respiratory tract, including the air sacs. Particles of greater than 5 microns are caught in the conjunctivae, nose and trachea down to the bifurcation. In the trachea, the virus is spread by the cillary action and by cell-to-cell infection. After initial multiplication at the introduction site, virulent virus is then carried to the spleen, liver, kidney and lungs. The virus eventually invades the brain, whereupon many birds start dying.

Symptoms of Newcastle disease are primarily respiratory and nervous. Gasping is common. Nervous symptoms include unilateral and bilateral paralysis of wings and/or legs, circular movements, bobbing/waving movements of the head and neck, and spasms of the wing, neck or leg muscles. General symptoms can include loss of appetite and decreased egg laying, often by as much as 40% or more.

Mortality can vary, depending on the properties of the virus involved and the immune status of the particular flock. Generally, those strains that kill quickly spread less between affected birds than those killing more slowly. In addition, a long asymptomatic carrier state has been presumed to occur in certain species of poultry such as chickens. The greatest risk of spreading the disease during an outbreak comes form movement of people and equipment. Due to centralization of many processes in the poultry industry, there is considerable traffic of personnel and equipment moving from one flock to another.

Many vaccines have now been developed to protect birds from the onset of Newcastle disease. Live antigen vaccines and attenuated antigen vaccines may be administered by eye or nose drop, or via spraying or drinking water. Inactivated vaccines can also provide protection, often at times without post-vaccinal respiratory reactions. Many of these are oil emulsion vaccines in which an oily adjuvant is utilized to enhance the immunogenic properties of the vaccine antigen. Vaccines may also be administered in ovo to developing chick embryos. In this way, better precision may sometimes be obtained.

U.S. Pat. Nos. 5,149,530; 5,250,298; 6,348,197; 5,750,111 and 5,733,556 each address the current state of the art as it relates to vaccines against the Newcastle disease virus. Some of the cited references further address combination vaccines, e.g. those containing one or more antigens directed to additional poultry ailments besides Newcastle disease.

Unfortunately, at present there appears to be no way to distinguish vaccinated members of a flock from those unvaccinated members that have-been afflicted with the virulent, "wild-type" version of Newcastle disease virus. In both instances, antibodies are produced in the animals' bodies. However, current vaccination immunogens against NDV induce antibodies that are very often indistinguishable from antibodies found after infection with virulent, infectious NDV.

What is therefore needed in the art is a new vaccine against the Newcastle disease virus. This vaccine should be safe and effective in preventing Newcastle disease when administered by eye or nose drop, or via spraying or drinking water, or in ovo to poultry. It should also permit poultry personnel to distinguish vaccinated members from unvaccinated members of the flock that have been afflicted with Newcastle disease. Development of a new vaccine should also permit the development of a reagent kit to assess whether an animal has been properly vaccinated, or has been infected with virulent Newcastle disease, or perhaps has been vaccinated with a more conventional NDV vaccine.

SUMMARY OF THE INVENTION

As part of the invention, there is provided a vaccine against Newcastle Disease virus, comprising about $10^0$–$10^9$ EID$_{50}$ of a mutant immunogen from the NDW strain of the Newcastle Disease virus, wherein the mutant immunogen lacks the antigenic binding site on the F glycoprotein recognized by the monoclonal antibody designated mAb 54.

Also provided is a mutant immunogen of Newcastle Disease virus identified as the strain deposited with the CNCM under accession number #I-2928. This mutant immunogen is suitable as a master seed virus in further developing an ND vaccine. The invention also provides for an immunogen of ND virus having the immunogenic characteristics of the deposited strain above.

There is also provided a method of protecting a poultry animal from Newcastle Disease, which comprises administering to the animal a vaccine containing about $10^0$–$10^9$ $EID_{50}$ of a mutant immunogen from the NDW strain of the Newcastle Disease virus, wherein the mutant immunogen lacks the antigenic binding site on the F glycoprotein recognized by the monoclonal antibody mAb 54.

The invention is also directed to a reagent kit for detecting inoculation via mutant immunogen against Newcastle Disease, comprising a standard NDV antigen and an illuminating antibody, wherein said illuminating antibody binds to said antigen in sera from inoculated birds, but does not bind to said antigen in sera from uninoculated birds.

There is further provided a method of generating a Newcastle Disease virus mutant immunogen useful in a vaccine against Newcastle Disease, which comprises growing Newcastle Disease virus in the presence of the monoclonal antibody designated mAb 54, such that said mutant immunogen develops and grows in the presence of said monoclonal antibody and is not neutralized by said monoclonal antibody. The mutant immunogen lacks the binding site on the F glycoprotein for an mAb54, and therefore is not neutralized by this antibody.

Also set forth is a mutant immunogen which is derived from the nucleotide sequence shown in Seq. ID No. 1. This partial nucleotide sequence codes for the F glycoprotein of the immunogen which lacks the binding site for the monoclonal antibody in mAb54. The amino acid sequence shown in Seq. ID No. 2 thereby represents the corresponding partial sequence of the F glycoprotein of Newcastle Disease virus.

The invention thereby also provides an immunogen of Newcastle Disease virus having the immunogenic characteristics of the mutant immunogen with the amino acid sequence shown in Seq. ID No. 2.

The invention further provides a mutant immunogen of Newcastle Disease virus in which the amino acid serine, normally found at position 157 in the wild-type NDW strains of virus, is replaced with arginine.

The invention additionally provides a reagent kit and method to assess whether a poultry animal has been vaccinated according to the invention as hereinafter described, or has been otherwise vaccinated using another NDV vaccine or has been infected with a wild-type ND virus.

Further objects and features of the invention will become apparent from the detailed description and the claims set forth herein below.

DETAILED DESCRIPTION OF THE PREFERRED EMBODIMENTS

It has now been discovered that a mutant immunogen derived from the Wiltenberg strain of the Newcastle Disease virus is useful in producing a marker vaccine against Newcastle Disease. The derived immunogen lacks the binding site for the monoclonal antibody designated in the art as "mAb 54", whereas all known existing ND virus strains possess a binding site for mAb 54. The characterization of mAb 54 as binding to the F fusion protein of NDV has been further described in. M.S. Collins et al. "Evaluation of Mouse Monoclonal Antibodies Raised Against an Isolate of the Variant Avian Paramyxovirus Type I Responsible for the Current Panzootic in Pigeons" in Arch. Virol. (1989) 104: 53–61.

The mutant immunogen lacking the binding site for mAb 54 may be generated by growing a live strain of the Newcastle Disease virus in the presence of the monoclonal antibody mAb 54. More preferably utilized is the virus strain available in the art as the Wiltenberg or NDW strain. A suitable NDW strain may be obtained from the CNCM (Collection Nationale de Cultures de Microorganismes) of the Institut Pasteur in Paris, France (25, Rue de Docteur Roux, F-75724 PARIS CEDEX), under accession number I-781, as further described in U.S. Pat. No. 5,149,530. The techniques for then growing and selecting the mutant immunogen may be found in Russell, P. H., *J. Gen. Virol.* 65, 795–798 (1984). Briefly described, the antibody mAb 54 will neutralize the growing Newcastle Disease virus by binding to the binding site on the virus recognized by the antibody, i.e. on the F glycoprotein portion. The exception will be certain escape mutants, or mutant immunogens which are formed without this binding site. These mutants thus escape neutralization and are able to grow and multiply.

It is these escape mutants, or mutant immunogens, which then form the basis of further vaccine development. The mutant immunogens may be further grown in suitable media, such as African green monkey kidney cells (VERO), for example. Immunoselection may be undertaken to further screen the derived mutant immunogens for reactivity with the antibody mAb54, as well as for virulence. Reversion to wild-type virus may be assessed using genetic and antigenic methods. The techniques described in Russell above may be helpful, as are other available techniques in the art.

A suitable mutant immunogen, i.e. a master seed virus mutant immunogen, has been deposited at the CNCM at the address above with the accession number I-2928 on Aug. 29, 2002. This especially preferred mutant immunogen, or mutagen, has now been further designated by Fort Dodge Animal Health as "p. 13." The p. 13 mutant immunogen is desirably subject to further serial passaging, as described below. The invention is also intended to encompass other mutant NDV immunogens which are prepared in substantially the same manner as set forth herein, and which have substantially the same immunogenic characteristics thereof.

A further characteristic of the mutant immunogen of ND virus of the invention is that the amino acid serine at position 157 in the wild-type NDW virus is replaced with arginine in the mutant version.

The mutant immunogen may be scaled up by serial passaging in poultry eggs, preferably embryonated poultry eggs, or in tissue culture using embryo fibroblasts from embryonated chicken eggs or VERO (African green monkey) cells, using available techniques. About two serial passages are contemplated by the invention, and up to about ten passages should prove useful. About four to about eight passages may be preferred by the skilled artisan. Embryonated chicken eggs are especially desirable for passaging the mutant immunogen.

The derived mutant immunogen as heretofore described is especially useful in providing immunological protection against Newcastle Disease. This mutant immunogen may be formulated into a vaccine against Newcastle Disease. A suitable vaccine will contain about $10^0$ to about $10^9$ $EID_{50}$ ("50% Egg Infectious Dose") of one or more mutant NDW immunogens, or immunogenically active component thereof, per dose. A more preferred range, especially for spray vaccination, is within the range of about $10^4$ to about $10^9$ $EID_{50}$. The aforesaid ranges may be further adjusted for administration via eye or nose drops, or via drinking water. For in ovo vaccination, a range of about $10^0$ to about $10^1$ $EID_{50}$ per dose may be utilized.

A dose is typically about 0.01 to about 10 mL, more preferably about 0.01 to about 1.0 mL (which ranges may be adjusted by the skilled artisan), of vaccine containing the heretofore described amount of mutant immunogen, as well as any adjuvant(s), excipient(s) and carrier, as further described below.

The vaccine of the invention may contain one or more suitable vaccine adjuvants and a pharmaceutically acceptable carrier. Suitable vaccine adjuvants can include compatible oils and oil emulsions available in the art. A pharmaceutically acceptable carrier can include water or saline, for example. Other excipients may also be included in the vaccine, for example, stabilizers and preservatives available in the pharmaceutical and vaccine veterinary art. These components, together with the mutant ND immunogen(s), may be admixed together to produce the final vaccine.

The vaccine of the invention is safe and effective for members of the poultry family, including chickens, turkeys, pheasants, guinea fowl, ducks, geese, bantams, pigeons and the like.

The vaccine of the invention containing mutant ND immunogen may also be formulated with additional vaccine antigens that provide immunological protection against other poultry ailments. For example, immunogens directed against Bursal disease, Marek's disease, and diseases caused by poultry herpes viruses may be utilized.

Administration of the vaccine of the invention is preferably via spraying, but may also be administered by eye or nose drop or via drinking water, all using methods available to the skilled artisan, as well as in ovo injection using suitable egg-injecting equipment, such as machines available from Embrex of North Carolina. Administration may be done in day-old eggs up to about 21 days of incubation. Inoculation once during the period of about days 10–18 may be particularly preferred. Thus, a method of protecting poultry from Newcastle disease will involve administering the vaccine as heretofore described in ovo to developing poultry.

Also included as part of the invention is a reagent kit and assay method of distinguishing poultry members that have been inoculated with the vaccine of the invention from those that have not been vaccinated and have been infected with the virulent, wild-type or "field" Newcastle disease virus, and from those that have been vaccinated with a conventional NDV vaccine which utilizes an immunogen containing the F fusion glycoprotein. Examples include ELISA, immunoperoxidase staining assay, Western blot, or any other suitable method available to technicians skilled in the art.

By way of non-limiting example, the kit can contain a "standard" NDV antigen (having the binding site on the F fusion glycoprotein recognized by mAb 54), as well as an illuminating antibody which also binds to this site on the standard antigen. The "illuminating" antibody will be labeled according to methods available in the art, and will thus "light up" and signal a color change upon binding to the standard antigen. The illuminating antibody can also be an anti-mouse antibody (since mAb 54 is derived from mice), for example, that has been labeled with an enzyme able to catalyze a color producing chemical reaction, as is available in the art. The anti-mouse antibody can bind to a second antibody (as part of the kit), which in turns binds to the binding site on the standard antigen (as in a standard sandwich assay).

In a further embodiment of the test kit and assay, there is also a competition-type assay in which an illuminating test kit antibody and a second test kit antibody would bind with a standard ND test kit antigen. Both antibodies would compete for the F glycoprotein binding site, and a differential reading would disclose positives and negatives.

A non-limiting method of testing poultry is briefly described as follows: Blood samples are taken from the poultry members to be investigated and are then individually tested. Poultry infected with a wild-type, field NDV, or which may have been inoculated with another ND strain still having the F glycoprotein binding site, will have developed internal antibodies against the site (F fusion glycoprotein) on the virus which is recognized by these antibodies. Upon addition of the test kit "standard" antigen to the sample, these internal antibodies will also bind to the same binding site on the standard antigen. This will preclude or significantly diminish the illuminating antibody from binding to this site on the standard antigen (as in a competition assay), and thus will preclude or significantly reduce a color change. On the other hand, poultry members that have been vaccinated according to the invention will lack the binding site on the F glycoprotein. Thus, no internal antibodies (mAb 54) will have been generated against this binding site. Upon addition of the reagent containing the standard antigen, the illuminating antibody can bind to the standard antigen, signaling a color change and an indication that the particular animal has been vaccinated according to the invention. Alternatively, a second test kit antibody can bind to the standard antigen, and the illuminating antibody can bind to this second antibody (as in a sandwich assay) to signal the color change.

In those instances where a poultry member has been vaccinated with a conventional NDV vaccine, antibodies against the F glycoprotein site may also have been generated but often to a different extent had the bird been otherwise infected with wild-type virus. In these cases, differentials in color changes can be noted to distinguish these animals.

Variations on the foregoing embodiments of the reagent kit and assay methods are also within the scope of the invention.

The following examples illustrate various preferred aspects of the invention, but should not be construed as limiting the scope thereof.

EXAMPLES

Example 1

Protocol

The following four-phase protocol briefly outlines a useful route in developing a marker vaccine against Newcastle Disease virus.

Phase 1

Determination as to whether antibodies are induced during natural infection with PMV1 (Paramyxovirus serotype 1, identified as NDV), to the antigenic site recognized by the antibody mAb54. Generate escape mutants lacking the antigenic site on the fusion protein recognized by mAb54, for further analyses.

Phase 2

Genetic identification of escape mutants lacking the antigenic site on the fusion protein recognized by mAb54.

Phase 3

Execution of escape mutant stability trials, checking for reversion to wild type or virulence.

Phase 4

Development and validation of an assay for the differentiation of antibodies to wild type and vaccine strains.

In further detail:

Phase 1

Examination of sera from birds infected naturally with PMV1 for antibodies to the antigenic site recognized by mAb54, using a competition binding assay.

Growing of the NDW strain of NDV on chick embryo fibroblast (CEF) cultures in the presence of mAb54.

Plaque purification of viruses produced in CEF and production of a stock of virus (designated mother virus stock) by limited passage in embryonated fowl's eggs.

Screening of escape mutants for reactivity with mAb54 using an immunoperoxidase (IPX) test.

Phase 2

Determination of the nucleotide sequence of the fusion protein of 'wild type' and escape mutants.

Execution of efficacy study of mother virus stock in one-day-old specific pathogen free ("SPF") chicks according to the protocol supplied (on completion of phase 1).

Selection of escape mutant(s) with absent/modified antigenic site as defined by mAb54 for phase 3.

Phase 3

Passaging of mother virus stock of selected escape mutant 2× in embryonated fowl's eggs to produce master (first pass) and working (second pass) seed viruses.

Production of vaccine virus for stability trials by 4× passage of working seed virus in embryonated fowl's eggs.

Confirmation of vaccine virus characteristics in IPX tests with mAb54 and by nucleotide sequencing.

Passaging of 'verified' vaccine virus 10× in embryonated fowl's eggs and confirmation of characteristics as described above.

Passaging of 'verified' vaccine virus 10× in CEF and confirmation of characteristics by IPX test.

Execution of in-vivo studies for reversion to virulence and wild type in one-day-old SPF chicks using a total of 10 passages.

Confirmation of the characteristics of virus reisolated from the $10^{th}$ in-vivo passage (or latest passage from which virus reisolated if less than 10) in IPX tests with mAb54 and by nucleotide sequencing.

Determination of the intracerebral pathogenicity index (ICPI) of the master seed, vaccine, in-vitro passaged (10×) vaccine and in-vivo passaged (10×, see above) vaccine viruses using one-day-old SPF chicks.

Phase 4

Production of monospecific antiserum in six-week-old chickens to 'wild type' and escape mutant strains of NDW. Antiserum to the latter would be raised using vaccine virus (see above).

Development of ELISA for the detection of NDV antibody to use as a kit assay to screen poultry sera for antibodies to 'wild type' and vaccine strains of NDV.

If appropriate (subject to progress with ELISA) modification of existing IPX test for NDV antibody, to use as a kit assay to screen poultry sera for antibodies to 'wild type' and vaccine strains of NDV.

Validation of selected test using known positive and negative sera to wild type strains of NDV.

Example 2

Methodology for Selection of Escape Mutants

The methodology as described in Russell, P. H., J. Gen. Virol. (1984) 65, 795–798, may be utilized. A summary of these procedures is as follows.

Use of 'Technomouse' to prepare a batch of the monoclonal antibody 617/54 (mAb54).

Cultivation of the NDW strain in 9-day-old embryonated fowl's eggs.

Determination of the neutralization index of mAb54. Assaying of the drop in viral infectivity with various dilutions of heat inactivated mAb by a micro-neutralization test. Reaction of equal volumes (50 ul) of virus and mAb for 2 hours at 37° C. and then adsorption to microwells of VERO cells. Execution of an IIP test and a count of the number of infected cells. Reduction in viral infectivity by $10^5$ or more is attempted.

Immunoselection of variant plaques. Incubation of an equal volume of virus and heat inactivated mAb at 37° C. for 2 hours. Dilution of this mixture $\frac{1}{10}$, $\frac{1}{100}$ and $\frac{1}{1000}$ in PBS/medium. Adsorption of each solution, including the non-diluted one, to two wells of confluent chick embryo fibroblasts (CEFs) (100 ul/well). After one hour at 37° C., addition of an agarose overlay containing a $\frac{1}{100}$–$\frac{1}{500}$ dilution of mAb and trypsin (2–5 ug/ml) to each well. Incubation of the plates at 37° C. in 5% $CO_2$.

After 3–4 days, visualization of individual plaques using the dye neutral red. 'Picking' of plaques using a Pasteur pipette pushed through the agarose to reach the cell sheet. Removal of a plug of agarose containing mutants is allowed to stand in PBS. Treatment of each preparation once again with an excess of mAb and repassaged in CEFs or embryonated fowl's eggs.

Growth of repassaged virus from each plaque in VERO cells with and without mAb 617/54. Screening of the escape mutants for reactivity with mAb 617/54 and polyclonal chicken antiserum using an immunoperoxidase (IPX) test.

Example 3

Efficacy Study of NDW Escape Mutant and 'Poulvac' Vaccine

Methods

Each of the two vaccinated groups (one mutant and the 'Poulvac' vaccine) comprised twenty-five day-old chicks.

There was one non-vaccinated control group of ten chicks.

The virus was passaged six times, in embryonated fowls' eggs, from plaque picked virus, and was used for all vaccinations with mutants.

Each vaccinated chick was intended to receive $10^{6.5}$ $EID_{50}$ in 0.5 ml demineralised water.

Birds were challenged using virulent NDV (Herts/33) by the intramuscular route, with a calculated dose of $10^{5.0}$ $ELD_{50}$ in 0.5 ml per bird.

Initially, titration of the mutant was carried out to determine the virus titre. This is shown in Table 1. The mutant p.13 was diluted to $10^{6.5}$ $EID_{50}/0.5$ ml and a total of 12.5 ml administered by coarse spray to the 25 chicks held in each isolator. The titre of the 'Poulvac' vaccine was $10^{10.02}$ $EID_{50}$ (provided by Fort Dodge Animal Health Holland, The Netherlands) per vial and was prepared so that each chick received $10^{6.5}$ $EID_{50}$ in 0.5 ml. Back titration of the viral preparation used to vaccinate the chicks was carried out in embryonated fowls' eggs immediately after vaccination. These titres were used to calculate the average estimated viral dose received per chick (Table 1). For challenge, there was a random mix of groups between two rooms. Each bird received a challenge dose of $10^{4.6}$ $ELD_{50}$ in 0.5 ml of Herts/33.

During the experiment, birds that were so sick they were unable to feed were destroyed. Records of sick birds that were able to feed and drink and survived until day fifteen of the experiment are detailed in Tables 2 and 3.

Results

Serum was taken from all surviving chicks, pre and post (15 days) challenge, for testing by haemagglutination inhibition (HI) with NDW virus.

The results of the efficacy study are summarized in Tables 2 and 3.

Virus Groups

Non-Vaccinated

The ten unvaccinated control chicks died within three days of challenge (100% mortality).

The sera from these birds were all negative in the HI test before challenge. 'Poulvac' vaccine One death (4% mortality) occurred on day four post-challenge among the chicks vaccinated with the 'Poulvac' vaccine. Virulent ND virus was recovered from this chick by the inoculation of homogenized brain tissue into embryonated fowls' eggs.

- Two other chicks showed clinical signs, one for a single day and the other until the end of the experiment.
- HI antibody titres ranged from 2–16 before challenge, 24 of these being less than or equal to 8. Post-challenge there was an increase in antibody titre in all birds (range 16–512).

Mutant p. 13

- None of the twenty-five chicks vaccinated with mutant p.13 died (0% mortality), although three of the birds displayed clinical signs.
- HI titres were 8 or less before challenge, but in most cases showed a significant increase, 32–1024 post-challenge.

TABLE 1

IMMUNIZING DOSE OF VACCINE VIRUSES PER BIRD

| Mutant number | Production method CEF or Vero cells | Virus titre $EID_{50}/0.1$ ml | Virus dose[a] |
|---|---|---|---|
| P13 | Vero | $10^{7.83}$ | $10^{5.95}$ |
| 'Poulvac' vaccine | — | $10^{10.02b}$ | $10^{6.6}$ |

[a]Calculated dose received by each chick in 0.5 ml.
[b]Viral titre per vial.

TABLE 2

SUMMARY DATA OF VACCINE EFFICACY STUDY USING NDW ESCAPE MUTANT VIRUS AND 'POULVAC' VACCINE.

| | Identification No. | HI 1 | HI/D 2 | Comments |
|---|---|---|---|---|
| Non-vaccinated Control group | 888 | $2^1$ | D | Died day 3 |
| | 889 | $2^1$ | D | Died day 2 |
| | 890 | $2^1$ | D | Died day 2 |
| | 891 | $<2^1$ | D | Died day 3 |
| | 892 | $2^1$ | D | Died day 3 |
| | 893 | $2^1$ | D | Died day 2 |
| | 894 | $2^1$ | D | Died day 2 |
| | 895 | $2^1$ | D | Died day 3 |
| | 896 | $2^1$ | D | Died day 3 |
| | 897 | $2^1$ | D | Died day 3 |
| Group vaccinated With 'Poulvac' vaccine | 601 | $2^3$ | $2^5$ | |
| | 602 | $2^2$ | $2^4$ | |
| | 603 | $2^3$ | $2^7$ | |
| | 604 | $2^2$ | $2^5$ | |
| | 605 | $2^2$ | $2^8$ | |
| | 606 | $2^3$ | $2^5$ | |
| | 607 | $2^3$ | $2^9$ | |
| | 608 | $2^3$ | $2^7$ | |
| | 609 | $2^2$ | $2^5$ | |
| | 610 | $2^2$ | $2^8$ | |
| | 611 | $2^3$ | $2^8$ | |
| | 612 | $2^2$ | $2^8$ | Sick day 9 onwards* |
| | 613 | $2^3$ | $2^7$ | |
| | 614 | $2^2$ | $2^6$ | |
| | 615 | $2^3$ | $2^8$ | Sick day 5 only |
| | 616 | $2^1$ | $2^6$ | |
| | 617 | $2^3$ | $2^5$ | |
| | 618 | $2^3$ | $2^6$ | |
| | 619 | $2^4$ | $2^6$ | |
| | 620 | $2^3$ | $2^6$ | |
| | 621 | $2^3$ | $2^5$ | |
| | 622 | $2^3$ | D | Died day 4 |
| | 623 | $2^2$ | $2^8$ | |
| | 624 | $2^2$ | $2^6$ | |
| | 625 | $2^3$ | $2^5$ | |
| Group vaccinated With Mutant p.13 | 476 | $2^3$ | $2^5$ | |
| | 477 | $2^3$ | $2^8$ | |
| | 478 | $2^2$ | $2^8$ | |
| | 479 | $2^2$ | $2^{10}$ | |
| | 480 | $2^3$ | $2^9$ | |
| | 481 | $2^3$ | $2^6$ | |
| | 482 | $2^3$ | $2^6$ | |
| | 483 | $2^2$ | $2^3$ | |
| | 484 | $2^2$ | $2^8$ | Sick day 7 to day 11 |
| | 485 | $2^2$ | $2^4$ | |
| | 486 | $2^2$ | $2^7$ | Sick day 5 onwards* |
| | 487 | $2^3$ | $2^6$ | |
| | 488 | $2^2$ | $2^8$ | |
| | 489 | $2^2$ | $2^6$ | |
| | 490 | $2^2$ | $2^8$ | |
| | 491 | $2^2$ | $2^5$ | |
| | 492 | $2^3$ | $2^5$ | |
| | 493 | $2^2$ | $2^5$ | |
| | 494 | $2^2$ | $2^8$ | |
| | 495 | $2^2$ | $2^5$ | |
| | 496 | $2^2$ | $2^5$ | |
| | 497 | $2^3$ | $2^4$ | |
| | 498 | $2^2$ | $2^5$ | |
| | 499 | $2^2$ | $2^5$ | |
| | 500 | $2^2$ | $2^9$ | Sick day 7 to day 10 |

TABLE 3

EFFICACY STUDY - PERCENTAGE MORTALITY IN EACH GROUP

| Group | Percentage mortality |
|---|---|
| Non-vaccinated | 100 |
| Poulvac' vaccine | 4 |
| p.13 | 0 |

Legend applicable to tables 2 and 3.
[1]HI titres before challenge expressed as the reciprocal of the dilution of serum completely inhibiting four haemagglutinating units of virus.
[2]HI titres post challenge of surviving birds. D = dead.
*Birds ataxic, some weight loss, moved only when disturbed but were able to feed and drink.

Example 4

Sequencing the Gene of the Fusion Protein ($F_O$) of NDW Escape Mutant and the 'Poulvac' Vaccine The mutant, passaged six times in embryonated fowls' eggs, was tested for reversion to 'wild type' by nucleotide sequencing using the automated sequencer ABI Prism™ 310 Genetic Analyzer. (The partial sequence for the F gene is shown—Seq. ID No. 1, along with the corresponding amino acid sequence shown in Seq. ID No. 2). A short sequence of the fusion protein F gene, across the region coding for the amino acid change at position 157, was determined for mutant p. 13. The amino acid sequences remained unchanged—the amino acid arginine still in place of the serine observed in the NDW 'wild type'. However, in mutant p.13 the codon for the arginine had changed from AGA to CGC.

The sequencing findings were supported by the IPX test. There appeared to be no evidence of mAb54 binding any of the mutants. However, NDW 'wild type' clearly bound this monoclonal antibody.

The entire gene sequence encompassing the reading frame of the precursor $F_o$ polypeptide was determined for the virus present in the 'Poulvac' vaccine. The sequence was identical to the master seed of NDW 'wild type' virus provided by Fort Dodge. However, there was a single difference between these sequences and that obtained from a sequence of NDW master seed which had received one further passage in embryonated fowls' eggs. This was a silent mutation at position 1195 of the gene.

Example 5

Further Efficacy Testing

Escape mutant p.13 was used for the following: A master seed virus (MSV), a working seed virus (MSV+1 passage), and an experimental vaccine (MSV+5 passages). The MSV was tested for reversion to virulence as prescribed in European Pharmacopoeia and tested for genetic stability after passages in eggs and in tissue culture on VERO cells. The experimental vaccine (MSV+5 passages) was tested for efficacy in commercial boilers. All tests indicated strong efficacy for the escape mutant (mutant immunogen) and vaccine of the invention.

Example 6

ND Marker Testing

Summary

In the present example, the possibility was investigated to distinguish sera from chickens vaccinated with ND marker strain p.13 from sera from chickens with antibodies against POULVAC® NDW vaccine (Fort Dodge Animal Health, Fort Dodge, Iowa and Weesp, the Netherlands) and sera from chickens with antibodies against virulent NDV. As previously noted, ND marker strain p.13 lacks the binding site for monoclonal antibody no. 54 (Mab#54).

Sera coded "MV" were obtained from chickens vaccinated with the ND marker strain p13; sera coded "FS" had been obtained from chickens with acute NDV infections; sera coded 9, 10, 11 and 12 were obtained from chickens vaccinated with POULVAC® NDW vaccine. As controls, serum from SPF chickens were included in the study and sera from chickens vaccinated with NDV B1 and challenged with NDV Herts 33. The study was done using an immunoperoxidase staining assay (IPX).

The MV coded sera showed some blocking of Mab#54, the SPF serum not. The reason for the blocking effect of the MV coded sera is not clear. While not being bound by any particular theory, it might be due to sterical hindrance by NDV antibodies binding adjacent to the binding site of Mab#54. It might be caused also by nonspecific binding activity. The FS coded sera averagely blocked binding of Mab#54, but there was some variety in results. The FS coded sera showed higher blocking activity than the MV coded sera. Blocking activity of the 9–12 coded sera was very clear and was clearly stronger than for the MV coded sera. There also was a clear difference between the MV coded sera and the NDV antiserum.

It was concluded that, using the IPX blocking test for Mab#54 it is possible to distinguish sera from chickens vaccinated with ND marker strain p13, from sera from chickens:
Experimentally infected with NDV,
Vaccinated with the live NDW vaccine.

Materials and Methods
  Materials
96 wells tissue culture plates with confluent monolayers of VERO cells.
Mab#54
NDV Ulster strain
10% buffered formalin
phosphate buffered saline (PBS)
SPF chicken serum
Antiserum against POULVAC® NDW batch
NDV positive serum was raised by infecting chickens with live avirulent B1, followed by challenge with virulent NDV Herts 33.
Field sera obtained from chickens suffering from acute Newcastle disease
Sera obtained after spray vaccination of chickens with the master seed virus of ND marker strain p13 followed by an intramuscular booster
Goat Anti-Mouse Immunoglobulin peroxidase conjugated antibody
Substrate solution A: 0.2 gr. Urea $H_2O_2$ in 10 ml sterile demineralized water
Substrate solution B: 0.1 gr. 3-amino-9-ethylcarbazole in 25 ml ethanol
Methods, Immunoperoxidase Staining Assay (IPX)
Infect plates with NDV Ulster—1/1000 and leave overnight
Add 50 ul of 10% buffered formalin per well for 20 minutes to fix the cells
Tip off formalin and wash the wells twice with 200 ul warmed 0.1 M PBS pH 7.2
Add 200 ul PBS and leave
Prepare a range of dilutions (½, 1/10, 1/25, 1/50 and 1/100 of the P13, field and. SPF sera) in PBS
Tip off PBS and pat plates dry
Add 100 ul of each dilution of serum to 10 wells of virus NDW and incubate at 37° C. for 45 minutes
Flick off serum dilutions, pat plate dry and wash all wells 3× with 200 ul PBS. Pat the plates dry.
Prepare a range of dilutions 1/500 to 1/10,000 of mAb 54 in PBS and 100 ul of each dilution to ½ wells containing antigen/ antibody for each dilution of test serum
Incubate plates at 37C for 45 minutes
Flick off mAbs and pat plate dry
Wash the wells 3 times with 200 ul PBS and pat dry
Add 100 ul of Goat Anti-Mouse Immunoglobulin peroxidase conjugated antibody to each well
Incubate for 50 minutes at 37C
Flick off conjugate and wash wells 3× with 200 ul PBS
Prepare final substrate solution by adding 0.1 ml of substrate solution A and 0.1 ml of substrate solution B to 9.8 ml PBS and mix
Add substrate, 100 μl per well, and leave for 15 minutes at room temperature
Wash the wells twice with PBS
Read the plates under the microscope
The presence of brown colored cells indicate binding of Mab#54

Results

Optimal Dilution of Mab#54

SPF serum and NDV antiserum were allowed to react with the antigen in different dilutions. Subsequently, Mab#54 also was allowed to react with the antigen in different dilutions. This test was done twice. The results of the first test are given in Table 4. (The results of the second test were greatly the same).

The results show that SPF antiserum does not block the binding of Mab#54 with the NDV antigen, although the reactivity is somewhat lower if a ½ dilution is used of the SPF serum. ½, ⅕ and 1/25 dilutions of the NDV positive antiserum block binding of Mab#54. Blocking is less at 1/50 dilution of the serum and almost no blocking is detected at a 1/100 dilution.

It can be concluded that the difference between SPF serum and NDV positive serum is most clear at serum dilutions of ⅕ and 1/25.

At the 1/50 dilutions and 1/100 dilutions of the NDV positive serum there was a decrease in reactivity at further dilutions of Mab#54. It was decided to use for further experiments a dilution of 1/2500 of Mab#54.

TABLE 4

REACTIVITY OF DIFFERENT DILUTIONS OF MAB#54 WITH NDV ANTIGEN AFTER PRE-INCUBATION WITH DILUTION SERIES OF SPF SERUM AND NDV POSITIVE ANTISERUM.

| Mab dilution | Dilution of the antiserum | | | | | | | |
|---|---|---|---|---|---|---|---|---|
| | ½ | ½ | ⅕ | ⅕ | 1/25 | 1/25 | 1/50 | 1/100 |
| SPF antiserum | | | | | | | | |
| 1/500 | ++ | ++ | +++ | +++ | +++ | +++ | +++ | +++ |
| 1/1000 | ++ | ++ | +++ | +++ | +++ | +++ | +++ | +++ |
| 1/2500 | ++ | ++ | +++ | +++ | +++ | +++ | +++ | +++ |
| 1/5000 | ++ | ++ | +++ | +++ | +++ | +++ | +++ | +++ |
| NDV antiserum | | | | | | | | |
| 1/500 | − | − | − | − | − | − | ++ | +++ |
| 1/1000 | − | − | − | − | − | − | + | ++ |
| 1/2500 | − | − | − | − | − | − | + | ++ |
| 1/5000 | − | − | − | − | − | − | − | + |

+ staining evident
++ strong staining
+++ very strong staining
− no evidence of staining Blocking of Binding of MAB#54 by Different Antisera In Table 5 results are given of blocking studies. Sera coded MV were obtained from chickens vaccinated with the ND marker strain p13. Sera coded FS were field sera obtained from chickens with acute NDV infections. Sera coded 9, 10, 11 and 12 were obtained from chickens vaccinated with POULVAC® NDW vaccine.

The results show that the SPF serum does not block binding of Mab#54, whereas the positive NDV serum blocks binding of Mab#54. The MV coded sera show some blocking activity. In the ½ dilution 2 of 8 sera block binding of Mab#54 and in the 1/10 dilution clear binding of Mab#54 is detected. There is great variety in blocking by the FS coded sera; FS1 clearly blocks binding of Mab#54, whereas FS6 hardly shows blocking activity.

The 9–12 coded sera all block binding of Mab#54, especially 11 and 12.

TABLE 5

REACTIVITY OF A 1/2500 DILUTION OF MAB#54 WITH NDV ANTIGEN AFTER PRE-INCUBATION WITH DILUTION SERIES OF VARIOUS CHICKEN SERA. PART A AND PART B WERE SEPARATE ASSAYS.

| Antiserum | ½ | ½ | 1/10 | 1/10 | 1/25 | 1/25 | 1/50 | 1/100 |
|---|---|---|---|---|---|---|---|---|
| PART A. Dilutions of polyclonal antisera | | | | | | | | |
| MV1 | − | − | + | + | ++ | ++ | +++ | +++ |
| MV2 | − | − | + | + | ++ | ++ | +++ | |
| MV3 | +w | +w | ++ | ++ | +++ | +++ | +++ | +++ |
| MV5 | +w | + | +++ | +++ | +++ | +++ | +++ | +++ |
| MV6 | + | + | +++ | +++ | +++ | +++ | +++ | +++ |
| MV7 | + | + | +++ | +++ | +++ | +++ | +++ | +++ |
| MV8 | +? | +? | ++ | ++ | +++ | +++ | +++ | +++ |
| MV9 | +w | +w | ++ | ++ | +++ | +++ | +++ | +++ |
| FS1 | − | − | − | − | + | + | +++ | +++ |
| FS3 | − | − | + | + | ++ | ++ | +++ | +++ |
| FS4 | −? | − | ++ | ++ | +++ | +++ | +++ | +++ |
| FS5 | +w | +w | ++ | ++ | +++ | +++ | +++ | +++ |
| FS6 | ++ | ++ | +++ | +++ | +++ | +++ | +++ | +++ |
| SPF | ++ | ++ | ++ | ++ | +++ | +++ | +++ | +++ |
| NDV | − | − | − | − | − | − | − | + |
| PART B. DILUTIONS OF POLYCLONAL ANTISERA | | | | | | | | |
| 9 | − | − | +w | +w | ++ | ++ | +++ | +++ |
| 10 | − | − | ND | ND | ND | ND | ND | ND |
| 11 | − | − | − | − | −? | −? | ++ | +++ |
| 12 | − | − | −? | −? | + | + | +++ | +++ |
| SPF | +++ | +++ | +++ | +++ | +++ | +++ | +++ | +++ |
| NDV | − | − | − | − | + | + | +++ | +++ |

+w = weak positive
−? = a very faint tinge of staining
+ = staining
++ = strong staining
+++ = very strong staining
ND = not done through insufficient serum Discussion The results of the MV, FS and 9–12 coded sera were evaluated as follows. + was given a value of 1, ++ was given a value of 2 and +++ was given a value of 3, and − was given a value of 0. Subsequently, an average value per serum was calculated. The same was done with the SPF serum and NDV positive serum.

The results are given in Table 6. The MV coded sera show some blocking of Mab#54, the SPF serum not. The reason for the blocking effect of the MV coded sera is not clear. Without being bound by any particular theory, it might be due to sterical hindrance by NDV antibodies binding adjacent to the binding site of Mab#54. It might be caused also by nonspecific binding of serum components.

Blocking activity of the FS coded sera averagely was stronger than for the MV coded sera. As indicated earlier there was some variety in results obtained with the FS coded sera. The FS coded sera were obtained from chickens with acute NDV symptoms. In some of these sera perhaps no NDV antibodies were present due to the short period between infection and collection of the sera. That might be an explanation for the variety in blocking activity between the individual sera.

Blocking activity of the 9–12 coded sera was strong. In comparison to that, the observed blocking by the MV coded sera was relatively weak. This difference was most clear at serum dilutions of 1/10 and 1/25. There also was a clear difference between the MV coded sera and the NDV antiserum.

TABLE 6

SUMMARIZED RESULTS OF BLOCKING STUDIES.

| Serum | Dilution of serum | | | | |
|---|---|---|---|---|---|
| | ½ | ⅒ | 1/25 | 1/50 | 1/100 |
| MV | 0.75 | 2.13 | 2.75 | 3.00 | 3.00 |
| FS | 0.60 | 1.60 | 2.40 | 3.00 | 3.00 |
| 9–12 | 0.00 | 0.33 | 1.00 | 2.67 | 3.00 |
| SPF | 2.50 | 2.50 | 3.00 | 3.00 | 3.00 |
| NDV | 0.00 | 0.00 | 0.50 | 1.50 | 2.00 |

Conclusion

Using the IPX blocking test for Mab#54 it is possible to distinguish sera from chickens vaccinated with ND marker strain p.13 from sera from chickens:

Experimentally infected with NDV,

Vaccinated with the live NDW vaccine.

While the invention has been described with particular reference to its preferred embodiments, it is expected that certain modifications thereto may be undertaken by the skilled artisan without departing from the invention's true spirit and scope as set forth in the specification and the following claims.

---

What is claimed is:

1. A vaccine against Newcastle Disease virus, comprising about $10^0$–$10^9$ EID$_{50}$ of a mutant immunogen from the NDW strain of the Newcastle Disease virus, wherein said mutant immunogen lacks the antigenic binding site on the F glycoprotein recognized by the monoclonal antibody designated Ab 54, wherein said mutant immunogen is identified as p. 13, and is deposited at the CNCM in Paris, France under accession number I-2928.

* * * * *

SEQUENCE LISTING

<160> NUMBER OF SEQ ID NOS: 2

<210> SEQ ID NO 1
<211> LENGTH: 1662
<212> TYPE: DNA
<213> ORGANISM: Paramyxovirus/Newcastle Disease Virus
<220> FEATURE:
<221> NAME/KEY: CDS
<222> LOCATION: (1)..(1662)

<400> SEQUENCE: 1

```
atg ggc tcc aga tct tct acc agg atc cca gta cct ctg atg ctg acc      48
Met Gly Ser Arg Ser Ser Thr Arg Ile Pro Val Pro Leu Met Leu Thr
1               5                   10                  15 gtc cgg gtc gcg ctg gca ctg agt tgc gtc tgt ccg aca agc tcc ctt      96
Val Arg Val Ala Leu Ala Leu Ser Cys Val Cys Pro Thr Ser Ser Leu
                20                  25                  30 gat ggc agg cct ctt gca gct gca ggg att gtg gtg aca gga gac aaa     144
Asp Gly Arg Pro Leu Ala Ala Ala Gly Ile Val Val Thr Gly Asp Lys
            35                  40                  45 gca gtc aac ata tac acc tca tct cag aca ggg tca atc ata gtc aag     192
Ala Val Asn Ile Tyr Thr Ser Ser Gln Thr Gly Ser Ile Ile Val Lys
        50                  55                  60 tta ctc cca aat atg ccc aaa gat aaa gag gcg tgt gca aaa gcc ccg     240
Leu Leu Pro Asn Met Pro Lys Asp Lys Glu Ala Cys Ala Lys Ala Pro
65                  70                  75                  80 ttg gag gcg tac aac agg aca ttg act act ttg ctc acc ccc ctt ggt     288
Leu Glu Ala Tyr Asn Arg Thr Leu Thr Thr Leu Leu Thr Pro Leu Gly
                85                  90                  95 gat tct att cgt agg ata caa gag tct gtg act aca tct gga gga ggg     336
Asp Ser Ile Arg Arg Ile Gln Glu Ser Val Thr Thr Ser Gly Gly Gly
                100                 105                 110 aaa cag gga cgc ctt ata ggc gcc att atc ggc ggt gca gct ctc ggg     384
Lys Gln Gly Arg Leu Ile Gly Ala Ile Ile Gly Gly Ala Ala Leu Gly
            115                 120                 125 gtt gca acc gct gca cag ata aca gca gct tcg gct ctg ata caa gcc     432
Val Ala Thr Ala Ala Gln Ile Thr Ala Ala Ser Ala Leu Ile Gln Ala
        130                 135                 140 aac caa aat gct gcc aac atc ctc cgg ctt aaa gag aga att gct gca     480
Asn Gln Asn Ala Ala Asn Ile Leu Arg Leu Lys Glu Arg Ile Ala Ala
145                 150                 155                 160 acc aat gag gct gtg cac gag gtc act gat gga tta tca caa cta gca     528
```

```
                    Thr Asn Glu Ala Val His Glu Val Thr Asp Gly Leu Ser Gln Leu Ala
                                        165                 170                 175 gtg gca gtt ggg aag atg cag caa ttt gtt aat gac cag ttt aat aaa        576
Val Ala Val Gly Lys Met Gln Gln Phe Val Asn Asp Gln Phe Asn Lys
                180                 185                 190 aca gct cag gaa ttg gac tgt ata aaa att acc cag cag gtt ggt gta        624
Thr Ala Gln Glu Leu Asp Cys Ile Lys Ile Thr Gln Gln Val Gly Val
            195                 200                 205 gaa ctc aac ctg tat cta act gaa ttg act aca gta ttc ggg cca caa        672
Glu Leu Asn Leu Tyr Leu Thr Glu Leu Thr Thr Val Phe Gly Pro Gln
        210                 215                 220 atc act tcc cct gcc tta acc cag ctg act atc cag gcg ctt tac aat        720
Ile Thr Ser Pro Ala Leu Thr Gln Leu Thr Ile Gln Ala Leu Tyr Asn
225                 230                 235                 240 cta gct ggt ggg aat atg gat tac ttg ttg act aag tta ggt gta ggg        768
Leu Ala Gly Gly Asn Met Asp Tyr Leu Leu Thr Lys Leu Gly Val Gly
                245                 250                 255 aac aac caa ctc agc tca tta att ggt agc ggc ctg atc acc ggc aac        816
Asn Asn Gln Leu Ser Ser Leu Ile Gly Ser Gly Leu Ile Thr Gly Asn
                260                 265                 270 cct att ctg tac gac tca cag act cag ctc ttg ggt ata cag gta acc        864
Pro Ile Leu Tyr Asp Ser Gln Thr Gln Leu Leu Gly Ile Gln Val Thr
            275                 280                 285 cta ccc tca gtc ggg aac ctg aat aat atg cgt gcc acc tac ttg gaa        912
Leu Pro Ser Val Gly Asn Leu Asn Asn Met Arg Ala Thr Tyr Leu Glu
        290                 295                 300 acc ttg tct gta agt aca acc aaa gga ttt gcc tca gca ctc gtc cca        960
Thr Leu Ser Val Ser Thr Thr Lys Gly Phe Ala Ser Ala Leu Val Pro
305                 310                 315                 320 aag gtg gtg atg aag gtc ggt tcc gta ata gaa gaa ctt gac acc tca       1008
Lys Val Val Met Lys Val Gly Ser Val Ile Glu Glu Leu Asp Thr Ser
                325                 330                 335 tac tgt ata gag acc gat ttg gat cta tat tgt aca aga ata gtg aca       1056
Tyr Cys Ile Glu Thr Asp Leu Asp Leu Tyr Cys Thr Arg Ile Val Thr
                340                 345                 350 ttc cct atg tct cct ggt att tat tcc tgt ttg agc ggc aat aca tcg       1104
Phe Pro Met Ser Pro Gly Ile Tyr Ser Cys Leu Ser Gly Asn Thr Ser
            355                 360                 365 gct tgc atg tac tcg aag act gaa ggc gca ctc acg acg ccg tac atg       1152
Ala Cys Met Tyr Ser Lys Thr Glu Gly Ala Leu Thr Thr Pro Tyr Met
        370                 375                 380 act ctc aaa ggc tca gtt att gcc aac tgt aag atg aca aca tgt aga       1200
Thr Leu Lys Gly Ser Val Ile Ala Asn Cys Lys Met Thr Thr Cys Arg
385                 390                 395                 400 tgt gca gac ccc ccg ggt atc ata tcg caa aat tat gga gaa gct gtg       1248
Cys Ala Asp Pro Pro Gly Ile Ile Ser Gln Asn Tyr Gly Glu Ala Val
                405                 410                 415 tct cta ata gat agg caa tca tgc aat gtc cta tcc tta gac gga ata       1296
Ser Leu Ile Asp Arg Gln Ser Cys Asn Val Leu Ser Leu Asp Gly Ile
                420                 425                 430 act ttg agg ctc agt ggg gaa ttt gat gca act tat caa aag aat atc       1344
Thr Leu Arg Leu Ser Gly Glu Phe Asp Ala Thr Tyr Gln Lys Asn Ile
            435                 440                 445 tca ata caa gat tct caa gta atc gtg aca ggc aat ctc gat atc tcg       1392
Ser Ile Gln Asp Ser Gln Val Ile Val Thr Gly Asn Leu Asp Ile Ser
450                 455                 460 act gag ctt ggg aat gtc aac aac tcg ata agt aat gct tta gat aag       1440
Thr Glu Leu Gly Asn Val Asn Asn Ser Ile Ser Asn Ala Leu Asp Lys
                465                 470                 475                 480
```

-continued

```
tta gag gaa agc aac agc aaa cta gac aag gtc aat gtc aaa ctg acc      1488
Leu Glu Glu Ser Asn Ser Lys Leu Asp Lys Val Asn Val Lys Leu Thr
                485                 490                 495 agc aca tcc gct ctc atc acc tat atc gtt tta act gtc ata tct ctt      1536
Ser Thr Ser Ala Leu Ile Thr Tyr Ile Val Leu Thr Val Ile Ser Leu
            500                 505                 510 gtt tgt ggt ata ctt agc ctg gtt cta gca tgc tac ctg atg tac aag      1584
Val Cys Gly Ile Leu Ser Leu Val Leu Ala Cys Tyr Leu Met Tyr Lys
        515                 520                 525 caa aag gcg caa cag aag acc ttg tta tgg ctt ggg aat aat acc ctg      1632
Gln Lys Ala Gln Gln Lys Thr Leu Leu Trp Leu Gly Asn Asn Thr Leu
    530                 535                 540 gat cag atg aga gcc act acg aaa atg tga                              1662
Asp Gln Met Arg Ala Thr Thr Lys Met
545                 550
```

<210> SEQ ID NO 2
<211> LENGTH: 553
<212> TYPE: PRT
<213> ORGANISM: Paramyxovirus/Newcastle Disease Virus

<400> SEQUENCE: 2

```
Met Gly Ser Arg Ser Ser Thr Arg Ile Pro Val Pro Leu Met Leu Thr
1               5                   10                  15

Val Arg Val Ala Leu Ala Leu Ser Cys Val Cys Pro Thr Ser Ser Leu
            20                  25                  30

Asp Gly Arg Pro Leu Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Gly Ala Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Arg Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270
```

```
Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Met Lys Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
    370                 375                 380

Thr Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg Gln Ser Cys Asn Val Leu Ser Leu Asp Gly Ile
            420                 425                 430

Thr Leu Arg Leu Ser Gly Glu Phe Asp Ala Thr Tyr Gln Lys Asn Ile
            435                 440                 445

Ser Ile Gln Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Cys Gly Ile Leu Ser Leu Val Leu Ala Cys Tyr Leu Met Tyr Lys
            515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```